US00PP31188P2

(12) United States Plant Patent
Danziger

(10) Patent No.: US PP31,188 P2
(45) Date of Patent: Dec. 3, 2019

(54) ***PORTULACA* PLANT NAMED 'DPORPZNYLW'**

(50) Latin Name: *Portulaca oleraea*
Varietal Denomination: DPORPZNYLW

(71) Applicant: Gavriel Danziger, Beit Dagan (IL)

(72) Inventor: Gavriel Danziger, Beit Dagan (IL)

(73) Assignee: Danziger 'DAN' flower Farm (IL)

( * ) Notice: Subject to any disclaimer, the term of this patent is extended or adjusted under 35 U.S.C. 154(b) by 0 days.

(21) Appl. No.: 16/350,238

(22) Filed: Oct. 16, 2018

(51) Int. Cl.
*A01H 5/02* (2018.01)
*A01H 6/30* (2018.01)

(52) U.S. Cl.
USPC ..... Plt./471
CPC ..... *A01H 6/30* (2018.05)

(58) Field of Classification Search
USPC ..... Plt./471
See application file for complete search history.

(56) References Cited

PUBLICATIONS

UPOV hit on *Portulaca* plant named 'DPORPZNYLW', QZ PBE 20182511, filed Oct. 4, 2018.*

* cited by examiner

*Primary Examiner* — Anne Marie Grunberg
(74) *Attorney, Agent, or Firm* — Cassandra Bright

(57) ABSTRACT

A new and distinct cultivar of *Portulaca* plant named 'DPORPZNYLW' is disclosed, characterized by large, bright yellow flowers on semi-upright, compact plants. Blooming begins early. The new variety is a *Portulaca*, normally produced as an outdoor garden or container plant.

2 Drawing Sheets

Figure 1:
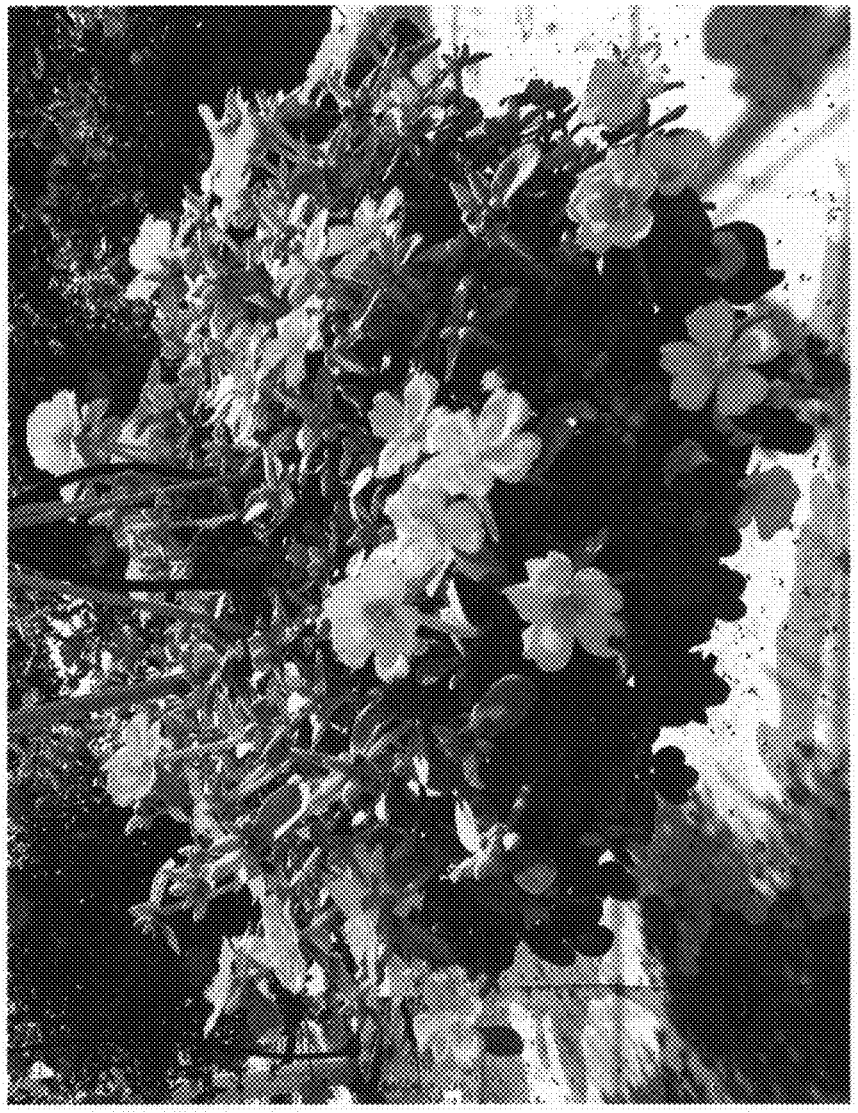

Latin name of the genus and species: *Portulaca oleraea.* Variety denomination: 'DPORPZNYLW'.

BACKGROUND OF THE INVENTION

The new *Portulaca* cultivar is a product of a planned breeding program by the inventor, Gavirel Danziger, at a commercial greenhouse in Moshav Mishmar Hashiva, Israel. The objective of the breeding program was to produce new *Portulaca* varieties. The open pollination resulting in this new variety was made during October of 2014.

The seed parent is the unpatented, propriety variety referred to as *Portulaca* 'PT-14-1152'. The pollen parent is unknown. The new variety was discovered in June of 2015 by the inventor in a group of seedlings resulting from the open pollination, in a greenhouse in Moshav Mishmar Hashiva, Israel. Date of first sale was Nov. 5, 2017, in Hungary. This sale was made directly by the inventor or one who obtained the claimed invention directly or indirectly from the inventor. This sale and all public disclosures made between Apr. 1, 2018 and the filing of this application fall within the exception allowed under 102(b)(1).

Asexual reproduction of the new cultivar 'DPORPZNYLW' was first performed by terminal vegetative cuttings during August of 2015, at a greenhouse in Moshav Mishmar Hashiva, Israel. Subsequent propagation by has shown that the unique features of this cultivar are stable and reproduced true to type in successive generations.

SUMMARY OF THE INVENTION

The cultivar 'DPORPZNYLW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPORPZNYLW' These characteristics in combination distinguish 'DPORPZNYLW' as a new and distinct *Portulaca* cultivar:

1. Semi-upright and compact habit.
2. Big bright yellow flowers.
3. Long blooming period—from Spring to Autumn.
4. Freely branching habit.
5. Early flowering.

PARENT COMPARISON

Plants of the new cultivar 'DPORPZNYLW' are similar to plants of the seed parent in most horticultural characteristics, however, plants of the new cultivar 'DPORPZNYLW' differ in the following;

1. 'DPORPZNYLW' has a very compact habit comparing to 'PT-14-1152'.
2. 'DPORPZNYLW' is open and flat. 'PT-14-1152' is conic (funnel-shaped).
3. Flowers of 'DPORPZNYLW' are larger than flowers of 'PT-14-1152'.
4. Flowers of 'DPORPZNYLW' are yellow, while flowers of 'PT-14-1152' are orange.

COMMERCIAL COMPARISON

Plants of the new cultivar 'DPORPZNYLW' can be compared to the unpatented commercial variety *Portulaca* 'DPAZYLWIMP'. These varieties are similar in most horticultural characteristics; however, 'DPORPZNYLW' differs in the following:

1. 'DPORPZNYLW' has more compact and dense habit compared to 'DPAZYLWIMP'
2. 'DPORPZNYLW' has bigger foliage than 'DPAZYLWIMP'.

Plants of the new cultivar 'DPORPZNYLW' can also be compared to the unpatented commercial variety *Portulaca* 'DPAZVIVIDY'. These varieties are similar in most horticultural characteristics; however, 'DPORPZNYLW' differs in the following:

1. 'DPORPZNYLW' has a brighter yellow flower color compared to 'DPAZVIVIDY'.
2. 'DPORPZNYLW' has more compact and dense habit compared to 'DPAZVIVIDY'
3. 'DPORPZNYLW' has larger flowers than 'DPAZVIVIDY'.
4. 'DPORPZNYLW' has brighter foliage compared to 'DPAZVIVIDY'.

BRIEF DESCRIPTION OF THE PHOTOGRAPHS

The accompanying photograph in FIG. 1 illustrates in full color a typical plant of 'DPORPZNYLW' grown in a greenhouse in Moshav Mishmar Hashiva, Israel, in a 20 cm basket. Age of the plant photographed is approximately 20 weeks from a rooted cutting.

Figure 2:
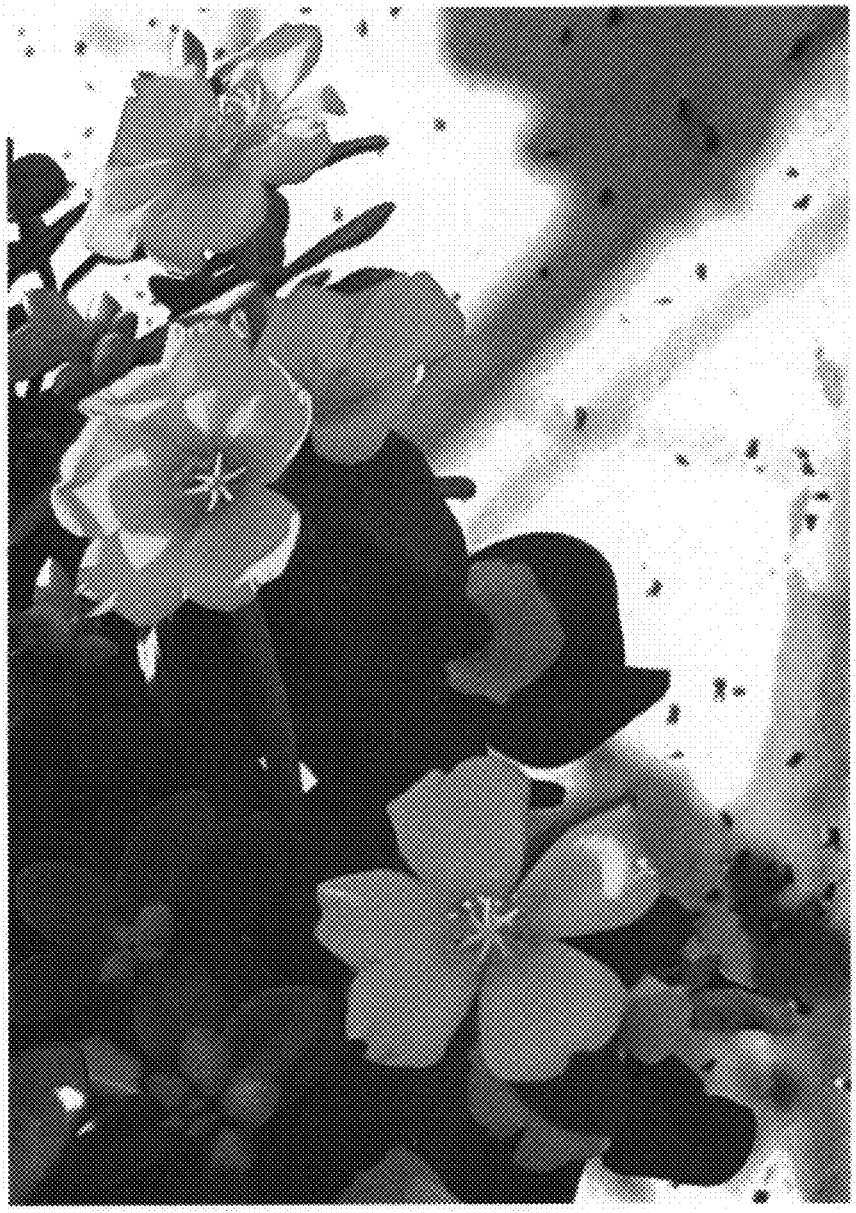

FIG. 2 illustrates a close up of the foliage and flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPORPZNYLW' plants grown in greenhouse in Moshav Mishmar Hashiva, Israel, under natural lighting. Measurements were taken during August of 2015. The plants were approximately 5.5 weeks from a rooted cutting in a 13 cm pot. The growing temperature ranged from 24° C. to 38° C. during the days, 14° C. to 26° C. during the nights. Measurements and numerical values represent averages of typical plant types.

Botanical classification: *Portulaca* 'DPORPZNYLW'.

PROPAGATION

Time to initiate roots: 7 to 10 days at approximately 24° C.

Root description: Fibrous, fine, close to RHS Yellow-White 158B in color, freely branching.

PLANT

Growth habit: Compact, semi-upright.

Pot size of plant described: 13 cm.

Height: Approximately 17 cm.

Plant spread: Approximately 22 cm.

Growth rate: Medium.

Branching characteristics:

Length of primary lateral branches: About 21 cm.

Diameter of lateral branches: About 0.5 cm.

Quantity of primary lateral branches: About 10 per 1 main stem.

Characteristics of primary lateral branches:

*Form.*—Glabrous.

*Diameter.*—About 0.3-0.4 cm.

*Color.*—Close to RHS Yellow-Green 144A and Greyed-Purple 183C.

*Texture.*—Smooth.

*Strength.*—Moderately strong.

Internode length: When close to the base: 2.5-2.7 cm. Close to tip: 2 cm.

FOLIAGE

Leaf:

*Arrangement.*—Opposite, simple.

*Quantity.*—Approximately 15 per branch.

*Average length.*—3.5 cm (young) and 4.5 cm (mature).

*Average width.*—2-2.5 cm.

*Shape of blade.*—Obovate, spatulate.

*Apex.*—Blunt (truncate).

*Base.*—Cuneate.

*Margin.*—Entire.

*Texture of top surface.*—Smooth.

*Texture of bottom surface.*—Smooth.

*Pubescence.*—Glabrous, succulent.

*Aspect.*—About 60-70°.

*Color.*—Young foliage upper side: Close to RHS 137A. Young foliage under side: Close to RHS 137D. Mature foliage upper side: Close to RHS 137B. Mature foliage under side: Close to RHS 137D.

*Venation.*—None.

*Petiole.*—Length: About 1.9 mm. Diameter: About 2 mm. Color: Close to RHS 144C. Texture: Smooth, glabrous.

FLOWER

Natural flowering season: Spring to Autumn.

Days to flowering from rooted cutting: 4 weeks.

Inflorescence and flower type and habit: Single flower, freely flowering habit.

Rate of flower opening: 3 days from bud to fully opened flower.

Flower longevity on plant: 1 to 2 days.

Persistent or self-cleaning: Self-cleaning.

Bud:

*Shape.*—Ovoid.

*Length.*—1 to 1.2 cm.

*Diameter.*—0.67 cm.

*Color.*—Close to RHS Yellow-Green 144B.

Flower size:

*Diameter.*—4.5 cm.

*Height.*—1.8 cm.

Corolla/petals:

*Arrangement.*—5 petals merged/fused at the base.

*Length.*—2.2 cm.

*Width.*—1.9 cm.

*Quantity.*—5 petals.

*Texture.*—Smooth, glabrous.

*Apex.*—Emarginate, retuse.

*Shape.*—Obovate with cuneate base.

*Margin.*—Entire.

*Aspect.*—Mostly upright.

Color:

*When opening.*—Upper surface: Close to RHS Yellow 6A. Lower surface: Close to RHS Yellow 6B.

*Fully opened*.—Upper surface: Close to RHS Yellow 7A. Lower surface: Close to RHS Yellow 6B.

Calyx/sepals:

*Quantity per flower*.—2 sepals per flower.

*Shape*.—Fused into a tubular calyx. Pointed tip.

*Length*.—0.7 cm.

*Width*.—0.6 cm.

*Apex*.—Acute.

*Base*.—Fused.

*Margin*.—Entire.

*Texture*.—Glabrous.

*Color*.—Upper Surface: RHS Yellow-Green 144A. Lower Surface: RHS Yellow-Green 144C.

Peduncle: None.

Fragrance: None.

REPRODUCTIVE ORGANS

Stamens:

*Number*.—Approximately 50.

*Filament length*.—Approximately 0.5 cm.

Anthers:

*Shape*.—Oval.

*Length*.—Less than 0.5 mm.

*Color*.—RHS Yellow 13A.

*Pollen*.—Color: RHS Yellow-Orange 17A. Quantity: Abundant.

Pistil:

*Number*.—1 per flower.

*Length*.—1.1 cm.

*Style*.—Length: 0.5 cm. Color: Near RHS Yellow 13A.

*Stigma*.—Shape: 6 branched stigma. Color: Near RHS Yellow 13A. Ovary Color: Near RHS Yellow-Green 144B.

OTHER CHARACTERISTICS

Seeds and fruits: Seeds are dark grey with a circular shape.

Disease/pest resistance: Neither resistance nor susceptibility observed. *Portulaca* is not typically susceptible to many diseases and pests. The most common diseases being typical root rots from over watering, or black stem, *Dichotomophthora portulaca*. The most common pest of *Portulaca* is Aphid.

Temperature tolerance: Will not tolerate temperatures below 7° C. High temperature tolerance near 40° C.

What is claimed is:

1. A new and distinct cultivar of *Portulaca* plant named 'DPORPZNYLW' as herein illustrated and described.

* * * * *